United States Patent
Hoctor et al.

(10) Patent No.: US 7,573,398 B2
(45) Date of Patent: Aug. 11, 2009

(54) SYSTEM AND METHOD OF COMMUNICATING SIGNALS

(75) Inventors: Ralph Thomas Hoctor, Saratoga Springs, NY (US); Richard Louis Zinser, Jr., Niskayuna, NY (US); Matthew George Grubis, New Berlin, WI (US); Neal John Seidl, New Berlin, WI (US)

(73) Assignee: General Electric Company, Niskayuna, NY (US)

( * ) Notice: Subject to any disclaimer, the term of this patent is extended or adjusted under 35 U.S.C. 154(b) by 408 days.

(21) Appl. No.: 11/171,173

(22) Filed: Jun. 29, 2005

(65) Prior Publication Data

US 2007/0002961 A1 Jan. 4, 2007

(51) Int. Cl.
*G01K 5/00* (2006.01)
(52) U.S. Cl. .................... 340/870.12; 340/870.06; 455/137; 455/139; 375/347
(58) Field of Classification Search ............ 340/870.12, 340/870.06; 455/137, 139; 375/347
See application file for complete search history.

(56) References Cited

U.S. PATENT DOCUMENTS

| | | | |
|---|---|---|---|
| 6,853,310 B2 | 2/2005 | Brinsfield | 340/870.41 |
| 2002/0118780 A1 | 8/2002 | Hurley et al. | 375/347 |
| 2005/0048993 A1 | 3/2005 | Ammar et al. | 455/502 |
| 2005/0114893 A1 | 5/2005 | Wetmore | 725/71 |

*Primary Examiner*—Albert K Wong
(74) *Attorney, Agent, or Firm*—Patrick K. Patnode

(57) ABSTRACT

A communication system is presented. The system includes one or more transmitters configured to transmit a signal, where each of the signals generated by the one or more transmitters corresponds to a respective frequency. Further, the system includes a plurality of receiver front-ends configured to receive the signal transmitted by each of the one or more transmitters. The system also includes a plurality of remodulator modules configured to translate each of the received signals to a signal having a respective intermediate frequency. In addition, the system includes a combining module configured to combine each of the signals having respective intermediate frequencies to generate a single composite signal. Also, the system includes a single analog-to-digital converter configured to process the composite signal and generate a digital output. Additionally, the system includes a digital signal processor module configured to extract the signal transmitted by each of the one or more transmitters.

21 Claims, 11 Drawing Sheets

SYSTEM AND METHOD OF COMMUNICATING SIGNALS

BACKGROUND

The invention relates generally to wireless communication, and more particularly to wireless transmission of data from mobile data acquisition units to a stationary central receiver.

Wireless services are increasingly ubiquitous and useful components in the global communication infrastructure, and wireless data telemetry is widely used because it allows collection of sensor information from any location in an antenna coverage area without reconfiguration of the communications infrastructure. An example of particular importance in medical practice is the wireless transmission of the electrocardiogram (ECG) data and other physiological monitoring signals acquired from patients in a hospital environment. Wireless telemetry allows these patients to be mobile, while vital signs of the patients are continuously monitored.

Many wireless telemetry systems are structured to employ frequency division multiple access (FDMA) schemes. In an FDMA transmission, each transmitter uses only a small band of contiguous frequencies, and frequency bands assigned to different transmitters are disjoint. All of the FDMA channels are typically contained within a larger band of frequencies, which is usually called "the channel".

Furthermore, wireless communication systems often operate in environments with severe fading due to multi-path propagation, which limits system performance. In the context of FDMA telemetry systems, such fading channels have the effect of transmitting each of the FDMA channels with a different power, and they are generally called multi-path fading channels. In general, this frequency response characteristic of the channel will change over time, due primarily to motion of the mobile transmitter, but also due to motion of other objects in the environment. In particular, one such frequency-selective fading environment is the indoor radio transmission environment. The wireless transmission of ECG telemetry data falls into this category, since it typically occurs inside a hospital building. A simple approach to overcoming the effects of fading is to provide for additional radiated power at the transmitter, over and above the power required to achieve the specified bit error rate (BER) at the specified range. Alternative schemes that do not depend on high transmit power may be advantageous in that they can, under some circumstances, translate into increased channel capacity. One such alternative scheme used to mitigate the effects of fading is the use of spatial antenna diversity.

Digital antenna arrays are of great interest to wireless communication systems. By utilizing spatial antenna diversity, the potential for performance improvement in wireless systems is vast. As will be appreciated, the spatial diversity approach employs multiple receive antennas to generate multiple copies of the same information-bearing signal. These copies are then combined in some fashion prior to demodulation of the received signal. This can help the system combat both multi-path fading and blockage of the radio frequency (RF) signal by obscuring objects (such as elevator shafts).

However, in a system that uses a spatial diversity scheme, it is often necessary to select the "best" receiving antenna field to use in the receiver. The selection criteria may be based on the highest signal power received or highest estimated signal-to-noise ratio (SNR). When using such "selection combining", the system performance may experience degradation due to loss of data experienced during antenna switching. Additionally, if the rate at which the antennas are switched is not high enough, changes in the environment may not be adequately tracked, resulting in temporary increases in the BER of the demodulated information.

A desirable alternative to antenna selection combining is coherent combination of the signals by the well-known technique of maximal ratio combining. In this combination scheme, signals are weighted by their measured received signal strength and the estimated noise power in the receive channel. This scheme results in a much better output signal-to-noise ratio than does selection combining. The most convenient form for such a combination is one in which all the signals are demodulated to their complex baseband representation prior to weighting and summation, although the combination may also be performed if the signals are modulated to a common intermediate frequency.

In order to coherently combine two received versions of a single FDMA channel, both of the antenna output signals at the two separate antennas must be channelized, translated to baseband, the required signal and noise powers must be estimated and the two signals "time-aligned", weighted and summed. In the past, the most practical approach to this sequence of operations was to perform the channelization in analog hardware, translate to baseband using analog mixers and local oscillators, digitize the result and perform the power estimation and summation in software or firmware. This approach requires multiple analog front-ends, one for each antenna. This is to be contrasted with selection combining, which requires only an analog switch to connect the selected antenna to the front-end hardware. It is because of this difference in implementation cost that selection combining is more commonly used than coherent combining.

More recently, the availability of very high speed analog-to-digital converters (ADCs) and digital signal processors (DSPs) has sparked interest in the use of software to perform many radio receiver functions that were formerly done in analog hardware.

It may therefore be desirable to develop an approach to coherent combination of signals in a FDMA telemetry radio that advantageously facilitates enhanced performance of the wireless communication systems in a multi-path fading environment.

BRIEF DESCRIPTION

Briefly, in accordance with aspects of the present technique a system is presented. The system includes one or more transmitters, where each of the one or more transmitters is configured to transmit a signal, and where each of the signals generated by the one or more transmitters corresponds to a respective frequency. Further, the system includes a plurality of receiver front-ends configured to receive the signal transmitted by each of the one or more transmitters. The system also includes a plurality of remodulator modules configured to translate each of the received signals to a signal having a respective intermediate frequency. In addition, the system includes a combining module configured to combine each of the signals having respective intermediate frequencies to generate a single composite signal. Also, the system includes a single analog-to-digital converter configured to process the composite signal and generate a digital output. Additionally, the system includes a digital signal processor module configured to extract the signal transmitted by each of the one or more transmitters.

In accordance with another aspect of the present technique, a method of communicating signals is presented. The method includes transmitting a signal via one or more transmitters, where each of the one or more transmitters is configured to transmit the signal at a respective frequency. Further, the method includes receiving the transmitted signal via a plurality of receiver front-ends. In addition, the method includes converting each of the received signals to a respective signal having a respective intermediate frequency. Additionally, the method includes combining each of the signals having respective intermediate frequencies to generate a single composite analog signal. The method also includes processing the composite analog signal via an analog-to-digital converter to generate a digital output signal. Furthermore, the method includes processing the digital signal via a digital signal processor module to extract the signal transmitted by each of the one or more transmitters. In addition, the method includes combining the individual copies of each of the transmitted signals to reconstruct the transmitted signal.

In accordance with yet another aspect of the present technique, a method of communicating signals is presented. The method includes receiving a transmitted signal at a plurality of receiving antennas. Further, the method includes processing each of the received signals via a bandpass filter. Additionally, the method includes amplifying each of the filtered signals via a low noise amplifier. The method also includes translating each of the filtered signals to a respective signal having a respective intermediate frequency. In addition, the method includes processing each of the signals having a respective intermediate frequency. Further, the method includes combining each of the processed received signals to generate a single composite signal.

In accordance with yet another aspect of the present technique, a method of communicating signals is presented. The method includes receiving a digital signal having a remodulated signal spectrum of a signal transmitted via one or more transmitters. In addition, the method includes extracting individual copies of the transmitted signal. The method also includes translating each of the individual copies to baseband via a numerically controlled oscillator and a mixer. Further, the method includes reducing sampling frequency of each of the individual copies via one or more stages of decimation filtering. Additionally, the method includes resampling each of the individual copies to align each of the individual copies in time. The method also includes combining the time-aligned copies. Further, the method includes processing the combined time-aligned copies via a detector to generate a single digital output signal.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Wireless communication systems are being increasingly employed in various fields. Further, wireless communication systems suffer from degradation of system performance as they often operate in environments with severe fading due to multi-path propagation. Multiple-antenna systems have been used to mitigate the problem of fading. In addition, spatial diversity schemes have been employed to enhance performance of wireless communication systems. However, the wireless communication systems using spatial diversity suffer from degradation of performance due to increased switching time between antennas, loss of data during antenna switching and higher BER. It may therefore be desirable to develop a robust technique that advantageously facilitates enhanced performance of the wireless communication systems. The techniques discussed herein address some or all of these issues.

Figure 1:
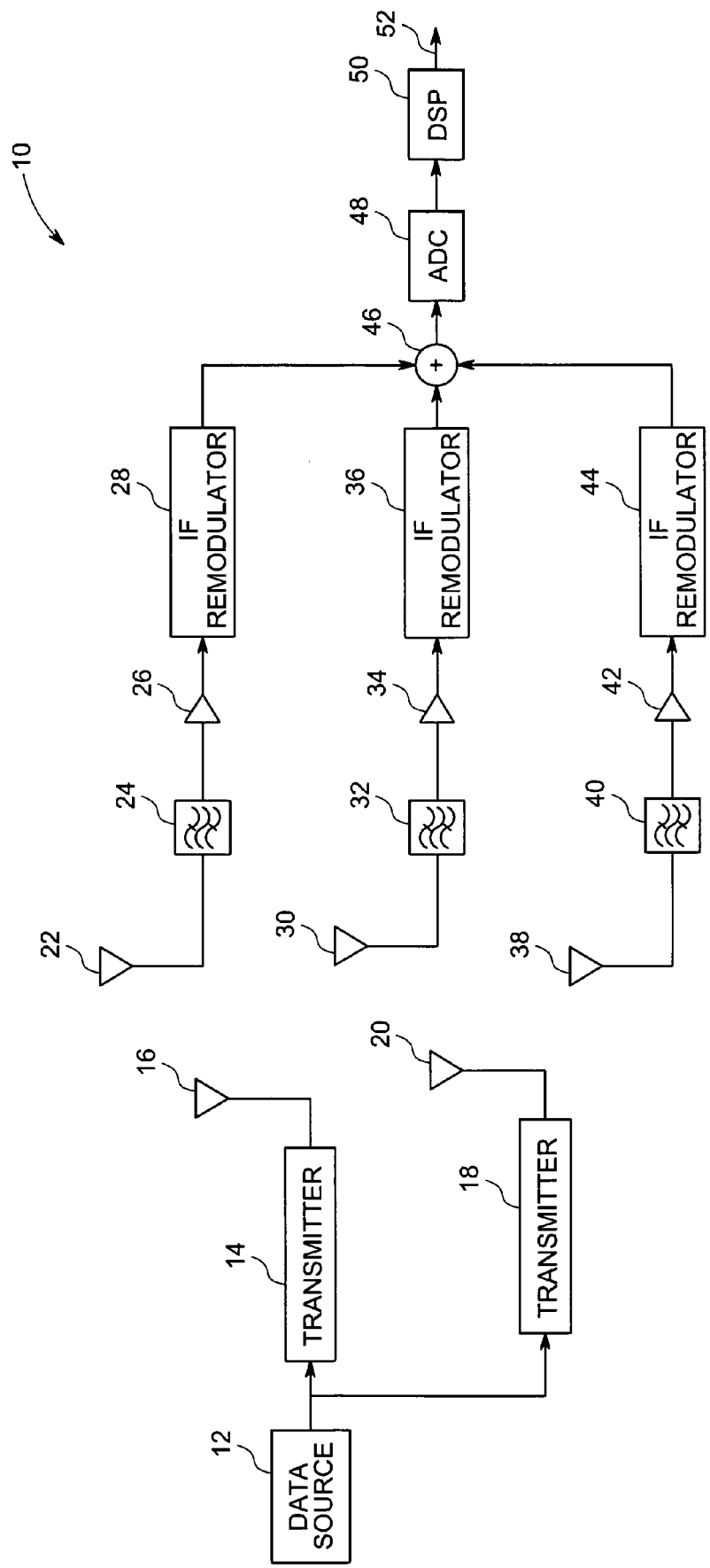
FIG. 1 illustrates a schematic diagram of a wireless communication system, according to aspects of the present technique.

Referring to FIG. 1, an exemplary wireless communication system 10, in accordance with aspects of the present technique, is illustrated. In the illustrated embodiment the wireless communication system 10 is shown as including a data source 12. In certain embodiments, the data source 12 may be different mobile devices, such as, for example, mobile cell phones or telemetry units attached to ambulatory patients. In one embodiment, the data generated by the data source 12 may include medical data such as, but not limited to, electrocardiogram (ECG) data, blood pressure data, blood oxygen level data, data from implantable medical devices, such as cardiac pacemakers, defibrillators, and blood-glucose monitors. In accordance with exemplary aspects of the present technique, the system 10 for communicating signals from a transmitter to a plurality of receivers is presented. However, as will be appreciated, a transmitting station may include one or more transmitters configured to transmit an information-bearing signal. The illustrated embodiment of FIG. 1 depicts a system 10 where the transmitting station is shown as including a first transmitter 14 and a second transmitter 18.

The data source 12 may be coupled to the transmitting station that may include a first transmitter 14 and a second transmitter 18. The first transmitter 14 may be coupled to a first transmitting antenna 16. Additionally, the second transmitter 18 may be coupled to a second transmitting antenna 20. It may be noted that figures are drawn for illustrative purposes and are not drawn to scale. Also, as will be appreciated, in certain other embodiments, the wireless communication system 10 may include more or fewer transmitters and transmitting antennas than illustrated in FIG. 1. The transmitters 14, 18 may be configured to transmit an information-bearing signal including data generated by the data source 12 via the respective transmitting antennas 16, 20.

The wireless communication system 10 may be configured to transmit an information-bearing signal via the first and second transmitters 14, 18. In other words, each of the first and second transmitters 14, 18 is configured to transmit the same signal generated by the data source 12, albeit at different frequencies. Accordingly, the first transmitter 14 is configured to transmit the information-bearing signal at a first frequency. Similarly, the second transmitter 18 is configured to transmit the same information-bearing signal at a second frequency, where the second frequency is different from the first frequency.

Additionally, the wireless communication system 10 may include a receiving station, where the receiving station may include a plurality of receiver front-ends. As used herein "receiver front-end" refers to a module that includes a receiving antenna, a bandpass filter and a low noise amplifier (LNA). The plurality of receiver front-ends may be configured to receive multiple observations of the same signal transmitted from a transmitting station. A first receiver front-end may include a first receiving antenna 22 configured to receive signals transmitted by the first and second transmitters 14, 18. Further, the first receiving antenna 22 may be coupled to the first surface acoustic wave (SAW) filter 24. The SAW filter 24 may be coupled to a first low noise amplifier (LNA) amplifier 26. In addition, the first LNA 26 is coupled to a first intermediate frequency (IF) remodulator module 28 which will be described in greater detail with reference to FIG. 3. Similarly, a second receiver front-end may include a second receiving antenna 30 that is coupled to the second SAW filter 32, which may in turn be coupled to a second LNA 34. The LNA 34 may be coupled to a second IF remodulator module 36. In a similar fashion, as illustrated in FIG. 1, a third receiver front-end may include a third receiving antenna 38 that is coupled to the third SAW filter 40. The third SAW filter 40 is coupled to a third LNA 42. The third LNA 42 may also be coupled to a third IF remodulator module 44. Also, as will be appreciated, in certain other embodiments, the wireless communication system 10 may include more or fewer receiver front-ends than illustrated in FIG. 1, and may include more or fewer receiving antennas than illustrated in FIG. 1.

As previously noted, the first transmitter 14 is configured to transmit the information-bearing signal at a first frequency. Similarly, the second transmitter 18 is also configured to transmit the same information-bearing signal, albeit at a second frequency, where the first frequency is different from the first frequency. In other words, two copies of the information-bearing signal generated by the data source 12 are transmitted by the first and second transmitters 14, 18 at two different frequencies. Further, the transmitters 14, 18 may also be configured to modulate the data to be transmitted by employing any suitable modulation technique. For example, the modulation techniques may include one of minimum shift keying (MSK) modulation, frequency shift keying (FSK) modulation, Gaussian minimum shift keying (GMSK) modulation, differential frequency shift keying modulation, or Gaussian frequency shift keying (GFSK) modulation.

As will be appreciated, each of the receiving antennas may be configured to receive signals transmitted from each of the transmitting antennas. In the illustrated embodiment, each of the receiver front-ends may then be configured to receive the transmitted data signals via the respective receiving antennas 22, 30, 38. Accordingly, in the illustrated embodiment of FIG. 1, each of the receiving antennas 22, 30, 38 is configured to receive the two copies of the transmitted information-bearing signal, albeit at different amplitudes and phases. Consequently, in the illustrated embodiment of FIG. 1, a total of six copies of the information-bearing signal is received at the receiving antennas 22, 30, 38.

The signals received at each of the receiving antennas 22, 30, 38 may be filtered via a corresponding SAW filter 24, 32, 40. Further, each of the filtered signals may be amplified via a corresponding antenna amplifier 26, 34, 42. In addition, the signals received at each of the receiving antennas 22, 30, 38 may be downconverted to a respective intermediate frequency via a corresponding IF remodulator module 28, 36, 44. The working of the IF remodulator modules 28, 36, 44 will be described in greater detail with respect to FIG. 3. A composite signal may then be generated by adding each of the downconverted signals produced by the IF remodulator modules 28, 36, 44 via an adder 46.

Current wireless communication systems are known to disadvantageously include a plurality of analog-to-digital converters, generally one analog-to-digital converter for each receiver, thereby disadvantageously resulting in increased cost, size, power consumption and complexity of the wireless communication systems. However, in a presently contemplated configuration, the wireless communication system 10 may advantageously include a single ADC 48. The single ADC 48 is configured to receive the composite signal generated by the adder 46 and generate a discrete time digital signal. The digital signal produced by the ADC 48 may then be processed by a DSP module 50 to generate a desired output 52.

In a presently contemplated configuration, a software defined radio or software radio may be employed by the DSP module 50 to process the digital signal generated by the ADC 48. Software-defined radio or software radio, as will be appreciated by one skilled in the art, is one of the emerging technologies for the future of wireless communication services. By employing the software radio, the associated receiver processing that was previously implemented in hardware may now be implemented via software, thereby changing the economics of deploying and operating wireless communication systems. The receiver may include a wideband ADC that captures all of the channels of the software radio node. The receiver then extracts, downconverts and demodulates the channel waveform using software on a general purpose processor. Thus, the software radio in part extends the evolution of programmable hardware, increasing flexibility via increased programmability. Operational details of the software radio 50 will be described in greater detail with reference to FIGS. 3-5.

The wireless communication system 10 illustrated in FIG. 1 may find application in a variety of wireless communication applications and systems. For example, the wireless communication system 10 may find application in cellular telephone systems, satellite transmissions and telemetry systems. In one embodiment, the wireless communication system 10 may be included in a medical telemetry system. As will be appreciated, the use of wireless communication systems in the medical market has given rise to numerous new possibilities enabling increased patient safety and mobility, improvements in quality of patient care, efficient hospital administration capabilities and overall cost reduction.

Figure 2:
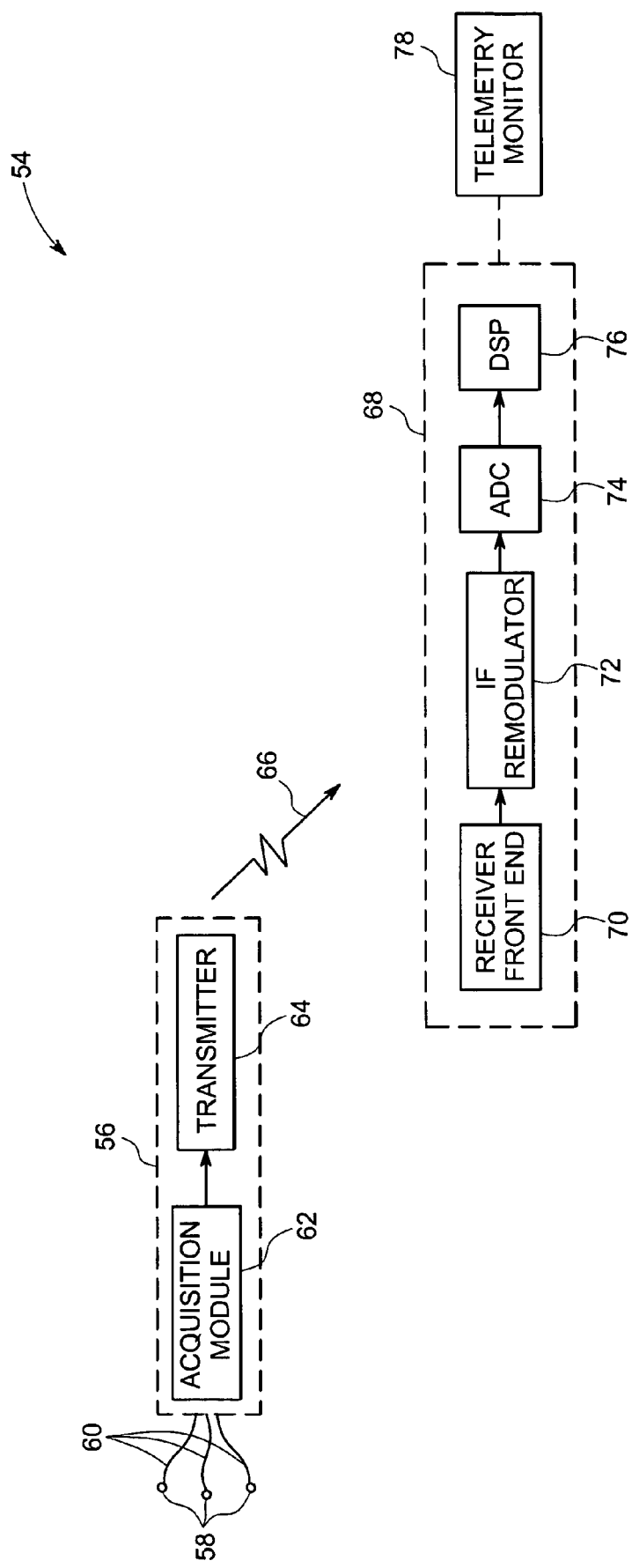
FIG. 2 is a schematic illustration of a telemetry system, according to aspects of the present technique.

FIG. 2 illustrates a telemetry system 54. In the illustrated embodiment, the telemetry system 54 may be the wireless communication system 10. As will be appreciated, wireless medical telemetry service (WMTS) is the remote monitoring of a patient's health where the wireless communication occurs between a patient-worn transmitter and a central monitoring station. In a presently contemplated configuration, the telemetry system 54 is shown as including a telemetry unit 56. The telemetry unit 56 is configured to acquire and monitor patient data from an ambulatory patient (not shown). In one embodiment, patient data may include ECG data, as previously noted. However, in other embodiments, the patient data may include one of pacemaker data, blood pressure data, blood oxygen level data, glucose monitor data, or data from medical alert pendants, for example.

Also, as shown in FIG. 2, the telemetry unit 56 may include a plurality of electrodes 58 that may be disposed on an ambulatory patient. A plurality of electrode wires 60 facilitates the acquisition of data from the electrodes 58 by an acquisition module 62. While wires 60 may be used in some implementations, other exemplary implementations may use wireless techniques, such as infrared or radio frequency transmission, for providing patient data from the electrodes 58 to the acquisition module 62. In addition, while electrodes 58 and wires 60 may be used to directly acquire data from a patient, the acquisition module 62 may instead acquire stored patient data from an archive site or data storage facility. Further, the acquisition module 62 may include circuitry to digitize the patient data, if needed, or such digitization may occur in another downstream module.

In addition, the telemetry unit 56 may include a transmitter 64. The transmitter 64 may be configured to wirelessly transmit the patient data acquired by the acquisition module 62. As will be appreciated, the telemetry unit 56 may include a plurality of transmitters. Also, as previously described with reference to FIG. 1, the transmitter 64 may employ the various modulation techniques to modulate the patient data prior to transmittal.

In certain embodiments, the acquisition module 62 may be configured to process the acquired patient data, such as ECG data. For example, the patient data may be conditioned into a desired signal or readable output that may then be transmitted by the transmitter 64 to a receiver. Alternatively, in some embodiments, the transmitter 64 may be configured to condition the patient data acquired by the acquisition module 62 and modulate the patient data into a modulated signal.

Subsequently, the transmitter 64 may transmit the modulated signal over a transmission channel 66. As will be appreciated, the Federal Communications Commission (FCC) has allocated interference-protected spectrum for use by licensed physicians, healthcare facilities and certain trained and supervised technicians in the 608-614 MHz, 1395-1400 MHz and 1427-1432 MHz frequency bands. In one embodiment, the transmitter 64 may modulate the patient data employing GFSK modulation technique and transmit the modulated data signal over the transmission channel 66 that may be configured to operate in a frequency range from about 608 MHz to about 614 MHz. Alternatively, in certain other embodiments, the transmission channel 66 may be configured to operate in a frequency range from about 1395 MHz to about 1400 MHz. In one embodiment, the transmission channel 66 may be configured to operate in a frequency range from about 1427 MHz to about 1432 MHz. Further, the transmission channel 66 may also be configured to support bands at 200 MHz and 400 MHz. In other words, the transmission channel 66 may be configured to operate in any permissible, suitable frequency range.

With continuing reference to FIG. 2, the telemetry system 54 may include a receiving module 68 that may be configured to receive the data signal transmitted via the transmission channel 66. In the illustrated embodiment, the receiving module 68 is shown as including a receiver front-end 70 that may be configured to receive the transmitted data signal. The receiver front-end 70 may include a receiving antenna, a SAW filter and a low noise amplifier, for example. However, as will be appreciated, the receiving module 68 may include a plurality of receiver front-ends. The received signal may then be downconverted to an intermediate frequency by an IF remodulator module 72. The signal may then be digitized by a single ADC 74 to form a single digital output signal. Alternatively, in the case of multiple receivers, a plurality of received signals may be downconverted to respective intermediate frequencies via respective IF remodulator modules 72 and combined via an adder (not shown) as described hereinabove to form a single composite analog signal. This composite signal may then be processed by the single ADC 74 to generate a digital output signal. Further, the digital output of the ADC 74 may be processed via a DSP module 76. The output of the DSP module 76 may then be communicated to a telemetry monitor 78.

Figure 3:
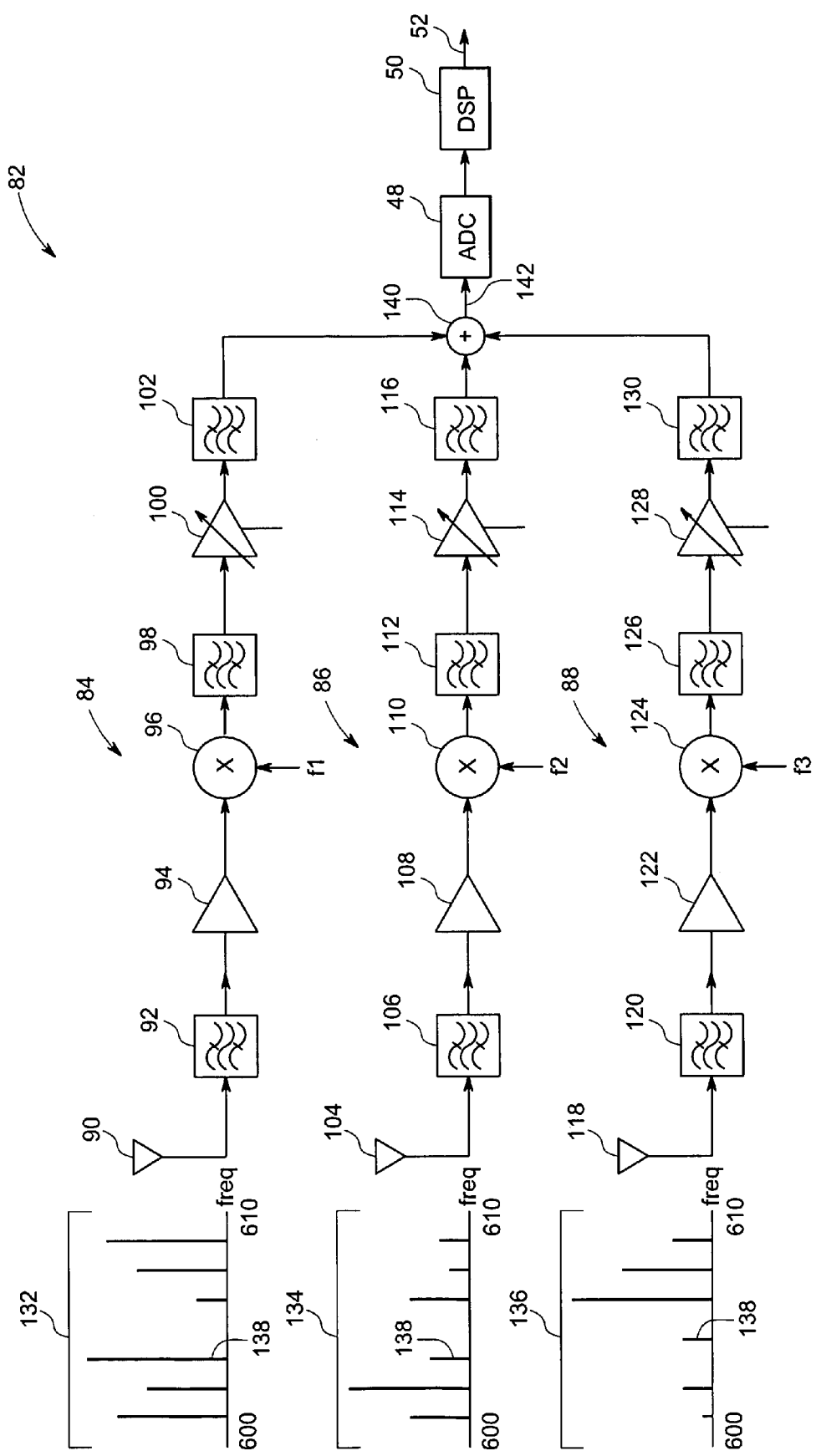
FIG. 3 is a schematic illustration of frequency multiplexing of received signals in the wireless communication system of FIG. 1, according to aspects of the present technique.

Multiple antenna receivers exploit diversity gain coherent combining methods in order to efficiently recover transmitted data. FIG. 3 illustrates an exemplary antenna diversity system 82 for combining a plurality of received signals received via a plurality of diversity branches. In the illustrated embodiment, the antenna diversity system 82 is illustrated as having a first diversity branch 84, a second diversity branch 86 and a third diversity branch 88, thereby representing a system for receiving and processing three sets of received signals. Further, in accordance with aspects of the present technique, frequency multiplexing of the received signals is employed to combine signals received from the three antenna diversity branches 84, 86, 88.

As will be appreciated, antenna diversity is defined as a technique that takes multiple observations of a signal transmitted from a transmitting station in order to recover that signal with greater accuracy, thereby enhancing overall signal reception. In other words, through antenna diversity, a receiving station obtains multiple observations of the same signal transmitted from a transmitting station. The redundancy built into the multiple observations may be advantageously employed to recover the transmitted signal with a higher degree of accuracy at the receiving station.

As previously noted, FIG. 3 illustrates the exemplary antenna diversity system 82 that employs frequency multiplexing to combine the signals received from three antenna diversity branches to be processed by a single ADC with sample frequency $f_s$. A first receiving antenna 90, a first surface acoustic wave (SAW) filter 92, a first low noise amplifier (LNA) 94, a first mixer 96, bandpass filter 98, a first variable gain amplifier 100 and bandpass filter 102 may be serially coupled to form the first diversity branch 84. The first receiving antenna 90 may be configured to receive signals transmitted from a transmitting station. For example, the first receiving antenna 90 may be configured to receive two copies of the information-bearing signal transmitted via transmitters 14, 18 (see FIG. 1).

Further, the first receiving antenna 90 may be coupled to a first SAW filter 92, where the first SAW filter 92 may be configured to function as a bandpass filter. Subsequently, an output of the first SAW filter 92 may be amplified via the first LNA 94. As will be appreciated, the first LNA 94 is typically a preamplifier that is configured to amplify very weak signals captured by the first receiving antenna 90. For maximum effectiveness, the LNA 94 is typically located as near to the receiving antenna 90 as possible.

In accordance with aspects of the present technique, the amplified signal may then be downconverted to an intermediate frequency (IF). In this embodiment, this downconversion may be achieved via a first mixer 96, which may be configured to mix the received RF signal with a signal, having a frequency $f_1$, from a first local oscillator. As will be appreciated, the first local oscillator facilitates generation of a stable RF frequency, where the local oscillator may be designed to operate at a frequency above (or below) the desired RF frequency by an amount equal to the IF frequency of the receiver. The received RF signal may be mixed via the mixer 96 with the stable RF signal generated by the first local oscillator to obtain a first intermediate frequency output signal.

This downconverted signal may then be filtered via a bandpass filter 98. The filtered signal may then be processed via the first variable gain amplifier 100. The processed signal may then be further processed via another bandpass filter 102. The output of the bandpass filter 102 is representative of the first received signal that has been downconverted to the first intermediate frequency.

In a similar fashion, a second receiving antenna 104, a second SAW filter 106, a second LNA 108, a second mixer 110, bandpass filter 112, a second variable gain amplifier 114 and bandpass filter 116 may be serially coupled to form the second diversity branch 86. As with the first receiving antenna 90, the second receiving antenna 104 may be configured to receive two copies of the transmitted signal. Additionally, the signals received at the second receiving antenna 104 may be processed along the second diversity branch 86 via the second SAW filter 106 and amplified by the second LNA 108. As previously described, the signals received at the second receiving antenna 104 may be downconverted to a second intermediate frequency with the aid of a stable RF signal, having a frequency $f_2$, from the second local oscillator. In this embodiment, the second intermediate frequency is different from that of the first intermediate frequency. The signal having the second intermediate frequency may be further processed via the bandpass filter 112, the second variable gain amplifier 114 and bandpass filter 116. Subsequent to this processing, a second signal having the second intermediate frequency is generated by the second diversity branch 86.

As described with reference to the first and second diversity branches 84, 86, a third receiving antenna 118, a third SAW filter 120, a third LNA 122, a third mixer 124, bandpass filter 126, a third variable gain amplifier 128 and bandpass filter 130 may be serially coupled to form the third diversity branch 88. The third receiving antenna 118 may be configured to receive two copies of the transmitted signal. Additionally, the signals received at the third receiving antenna 118 may be processed along the third diversity branch 88 via the third SAW filter 120 and amplified by the second LNA 122. As previously described, the signals received at the third receiving antenna 118 may be downconverted to a third intermediate frequency with the aid of a stable RF signal, having a frequency $f_3$, from the third local oscillator. In this embodiment, the third intermediate frequency is different from that of the first and second intermediate frequencies. The signal having the third intermediate frequency may be further processed via the bandpass filter 126, the second variable gain amplifier 128 and bandpass filter 130. Subsequent to the processing, a third signal having the third intermediate frequency is generated by the third diversity branch 88.

Reference numerals 132, 134 and 136 represent the same set of transmitted signals as received by the first, second and third receiving antennas 90, 104, 118 respectively, albeit at different amplitudes and phases. The signals 132, 134, 136 are for illustrative purposes and are not drawn to scale. Each vertical line in the spectra 132, 134, 136 is representative of a narrowband output of a single transmitter. For example, reference numeral 138 represents the information-bearing signal transmitted by a single transmitter, such as transmitter 14 (see FIG. 1). It may be noted that the signal 138, representative of the signal transmitted by the first transmitter 14, is received at the first, second and third receiving antennas 90, 104, 118 at different amplitudes and phases.

As described hereinabove, each of the received signals 132, 134, 136 is downconverted to a respective intermediate frequency via a respective diversity branch 84, 86, 88. In other words, these downconverted signals having respective intermediate frequencies have been translated to a different portion of the baseband spectrum. The donwconverted signals may then be added via an adder 140 to generate a single composite analog signal 142. In one embodiment, the composite analog signal 142 may have a bandwidth in a range from about 30 MHz to about 62.5 MHz.

Figure 4:
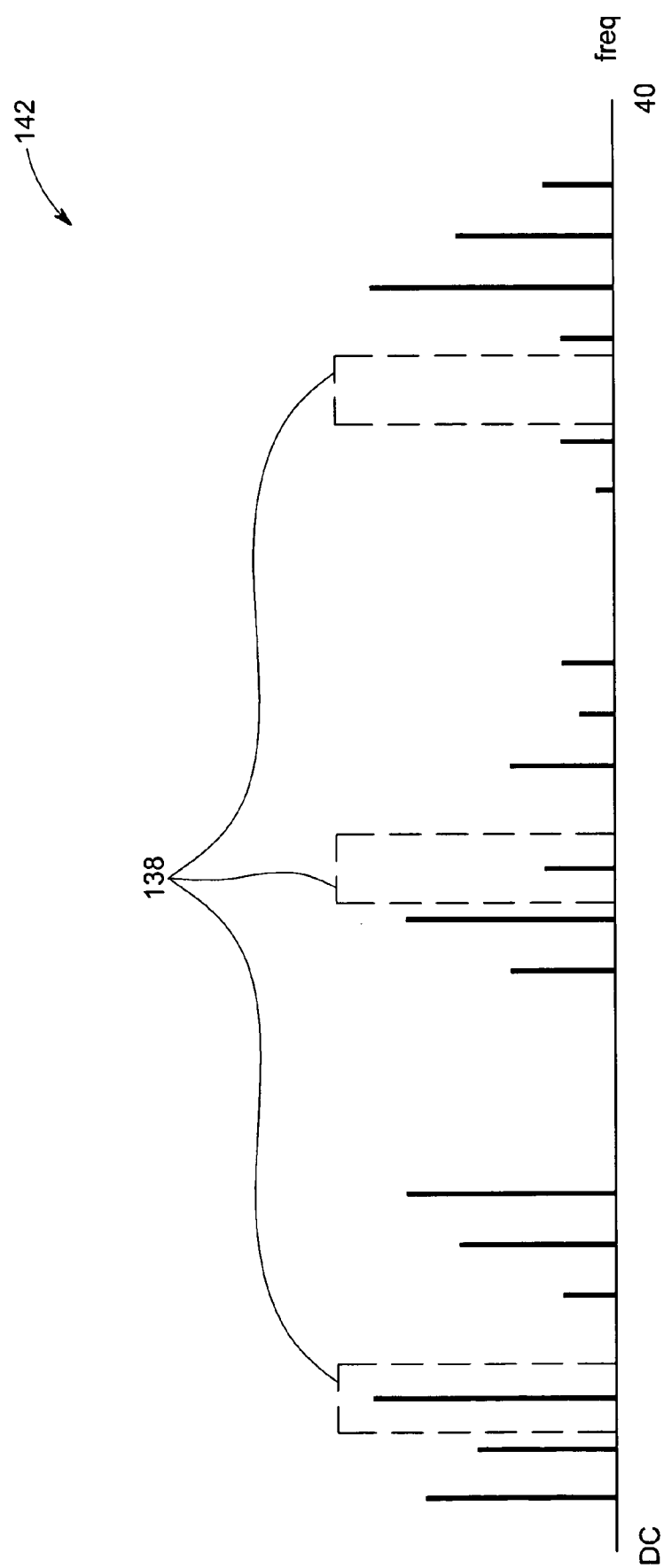
FIG. 4 is a schematic illustration of a composite signal, according to aspects of the present technique.

The composite signal 142 is illustrated in FIG. 4. In accordance with exemplary aspects of the present technique, the three copies of the transmitted signals 132, 134, 136 have been translated to a different portion of the baseband spectrum and are illustrated in FIG. 4. It may be noted that, in one embodiment, the composite signal 142 may have a bandwidth of 40 MHz.

With returning reference to FIG. 3, the composite signal 142 may then be processed via the single ADC 48. As previously described, the ADC 48 is configured to convert the composite signal 142 into a digital signal. In one embodiment, the ADC 48 may include an ADC that runs at a substantially high rate. For example, the ADC 48 may run at a rate in a range from about 60 MHz to about 125 MHz. Subsequently, the digital signal output from the ADC 48 may be processed via the DSP module 50 to generate the desired output 52.

Figure 5:
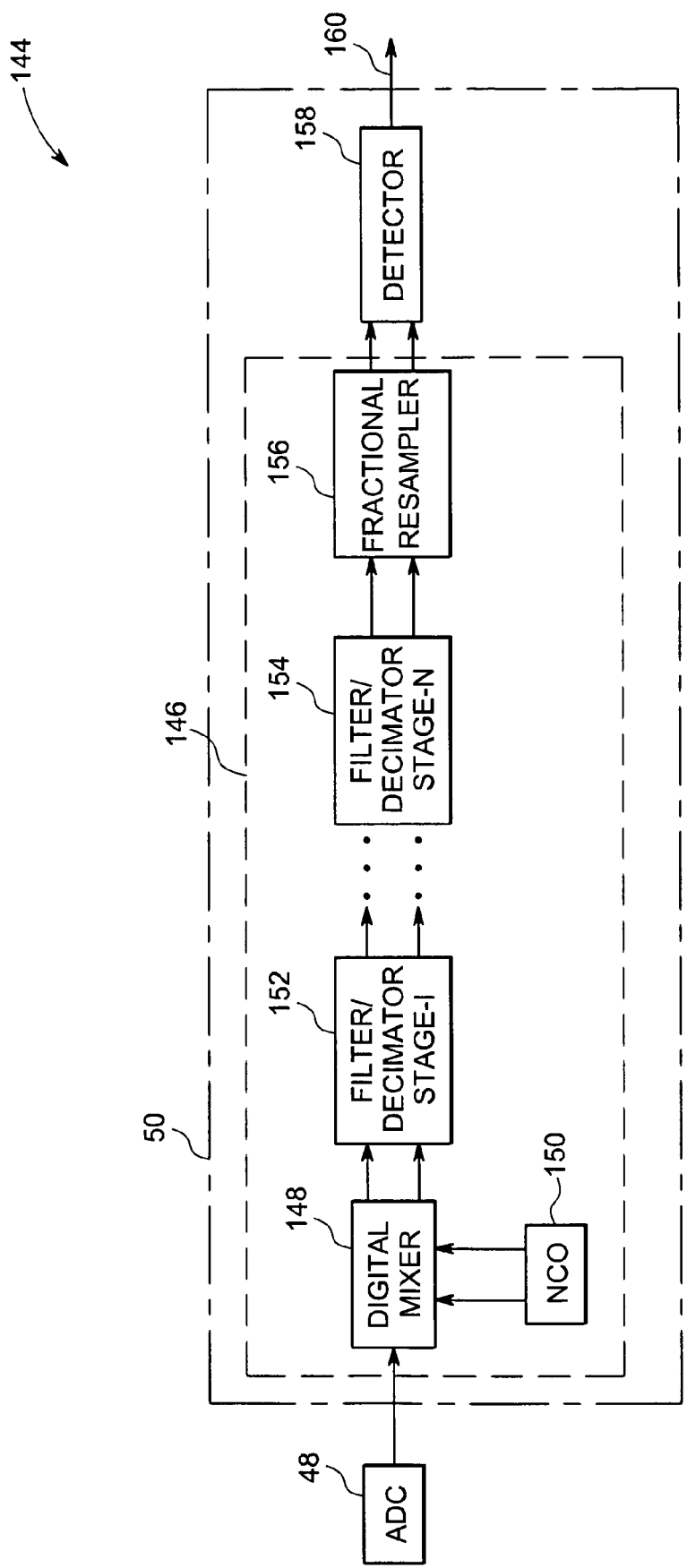
FIG. 5 illustrates the DSP module of FIG. 3 in greater detail.

As previously described, in accordance with exemplary aspects of the present technique, the DSP module 50 includes a software defined radio or software radio. FIG. 5 illustrates an exemplary embodiment of the architecture 144 of the software radio 50 of FIG. 1 in greater detail. In a presently contemplated configuration, the software radio 50 may include a digital downconverter 146 and a detector module 158. The software radio 50 may be configured to channelize the composite signal 142 into lower rate discrete signals, where each of the lower rate discrete signals is representative of a single baseband of the signal transmitted via a transmitter. Typically, the bandwidth of these lower rate discrete signals is on the order of tens of Kilo Hertz (KHz).

Accordingly, the software radio 50 may be configured to extract each of the individual narrowband copies of a signal transmitted by a given transmitter, such as transmitter 14 (see FIG. 1), translate the individual copies to DC and then decimate the corresponding sample rate of each individual signal from a higher sampling rate associated with the ADC 48 to a lower sampling rate, depending on the transmission rate and type of modulation used. For example, in one embodiment, the sampling rate of the ADC 48 may be 100 MHz. Accordingly, the software radio 50 may be configured to decimate the sampling rate of each individual signal from 100 MHz to a sampling rate in a range from about 20 KHz to about 50 KHz. The operation of the software radio 50 illustrated in FIG. 5 is described hereinafter.

As previously noted, a generic architecture of the software radio 50 is illustrated in FIG. 5. The software radio 50 may be configured to extract the individual copies of the transmitted signal, translate the individual copies to DC and decimate the sampling rate of these individual copies to a lower rate. The "channelization" process may be achieved via the use of a complex numerically controlled oscillator, a complex digital mixer and one or more stages of decimation filtering.

As previously noted, the software module 50 includes a digital downconverter 146. The digital downconverter 146 includes a numerically controlled oscillator 150 that may be configured to function as a tuning device. Further, a complex digital mixer 148 may include a set of multipliers and may be configured to translate the desired center (carrier) frequency to DC. In other words, the numerically controlled oscillator 150 and the mixer 148 may be configured to translate the desired narrowband signal to baseband in-phase (I) and quadrature (Q) signals. Additionally, the digital downconverter 146 includes one or more stages of decimation filter that is configured to provide selectivity and reduce the sampling frequency to audio rates. In other words, the several stages of decimation and filtering may be configured to eliminate undesirable signals and to reduce the sampling rate to an appropriate frequency for baseband operation. In the illustrated embodiment of FIG. 5, the digital downconverter 146 is shown as having a first filter/decimator stage 152 and a $N^{th}$ filter/decimator stage 154. In one embodiment, the illustrated architecture may be configured to operate in real time at an input sampling rate of 100 MHz and an output sampling rate of 50 KHz. Hence, the illustrated embodiment has a decimation ratio of 2000, for example.

The translation operation performed by the numerically controlled oscillator 150 and complex mixer 148 may be followed by one or more stages of decimation filtering to reduce the sampling rate. As will be appreciated, a decimation filter selects a desired channel in the presence of both strong adjacent channel interferes and quantization noise from the digitization process. In one embodiment, an $N^{th}$ order Cascaded-Integrator-Comb (CIC) filter may be employed to perform the decimation process. The extremely simple design associated with CIC filters advantageously allows high-speed operation in almost any architecture.

The signals processed via the decimation filter may then be processed by a filter such as a finite impulse response (FIR) filter. The FIR filter may be employed as a final "clean up" device that removes the alias products between the final passband edge and half the CIC output sampling frequency. Further, the FIR filter may also be configured to provide adjacent channel rejection.

Consequent to processing via the digital downconverter 146, three different versions of the same signal are available. These three different versions of the same signal may then be optimally combined while maintaining minimum BER. Accordingly, correct time-alignment of the received signals may be desirable in combining the three versions of the same signal. Because of the narrowband nature of the downconverted signal, and the desire to minimize the number of samples per symbol (lower processing requirements), time-alignment may require time shifts less than one sample period. This may be achieved with a "fractional delay filter" such as the fractional sampler 156, which may be easily implemented with a FIR architecture.

These time-aligned signals may then be combined to generate one signal representative of the signal transmitted via a given transmitter. In one embodiment, the combining step may take place prior to a detection process. Alternatively, the combining step may be performed during the detection process. In one embodiment, the decision about how to process the signal components may be dependent on the respective estimated signal-to-noise ratio values of the signal components having first, second and third intermediate frequencies. Alternatively, in certain other embodiments, the decision may be based on other criteria such as the estimated signal power of the signals having the first, second and third intermediate frequencies. In certain other embodiments, the three copies of the transmitted signal may be coherently combined via maximal ratio combining. As will be appreciated, the maximal ratio combiner linearly weights the signals according to estimates of the signal-to-noise ratio for each version of the signal. The weighted signals are then added together.

It should be noted that the software radio 50 may be designed to run multiple instantiations of the processing described hereinabove. In other words, a separate numerically controlled oscillator, complex mixer, filter, decimator chain is employed for each narrowband signal to be demodulated. Referring to FIGS. 3-4, three copies 132, 134, 136 of the transmitted signal have been distributed over the composite signal 142. Accordingly, three instantiations of the processing described with reference to FIG. 5 may be employed to simultaneously downconvert the respective signals to baseband.

The signals may subsequently be processed via a detector module 158. In one embodiment, the detector module may employ a suitable demodulation technique to reproduce the transmitted data signals. For example, the demodulation techniques may include one of a minimum shift keying (MSK) demodulation, frequency shift keying (FSK) demodulation, Gaussian minimum shift keying (GMSK) demodulation, differential frequency shift keying demodulation, offset quadrature phase shift keying (OQPSK) demodulation, or Gaussian frequency shift keying (GFSK) demodulation.

As previously noted, the software radio 50 may also include a detector module 158. The detector module 158 may include detection algorithms that may be implemented in a programmable processor such as a personal computer (PC) processor or a DSP chip. These detection algorithms may be configured to convert the I and Q sample streams to a single digital output signal 160. The output signal 160 may then be played out through a narrowband digital-to-analog converter with appropriate reconstruction filtering. For example, if the transmitted signal includes ECG data, the output signal includes the corresponding ECG waveform.

The illustrated embodiment of FIG. 5 utilizes three single-conversion front-ends, one for each diversity branch. Each front-end has a respective bandwidth $BW_1$, $BW_2$ and $BW_3$ and a respective intermediate frequency, $f_{I1}$, $f_{I2}$, and $f_{I3}$. In one embodiment, $f_{I1}$, $f_{I2}$ and $f_{I3}$ may be chosen to satisfy:

$$N_1(f_{I1}, f_s) = f_1$$

$$N_2(f_{I2}, f_s) = f_2$$

and $$N_3(f_{I3}, f_s) = f_3 \qquad (1)$$

where $N_1(f_{I1}, f_s)$ is a function mapping the frequency f to its image in the first Nyquist zone of the ADC and $f_s$ is the sampling frequency.

Figure 6:
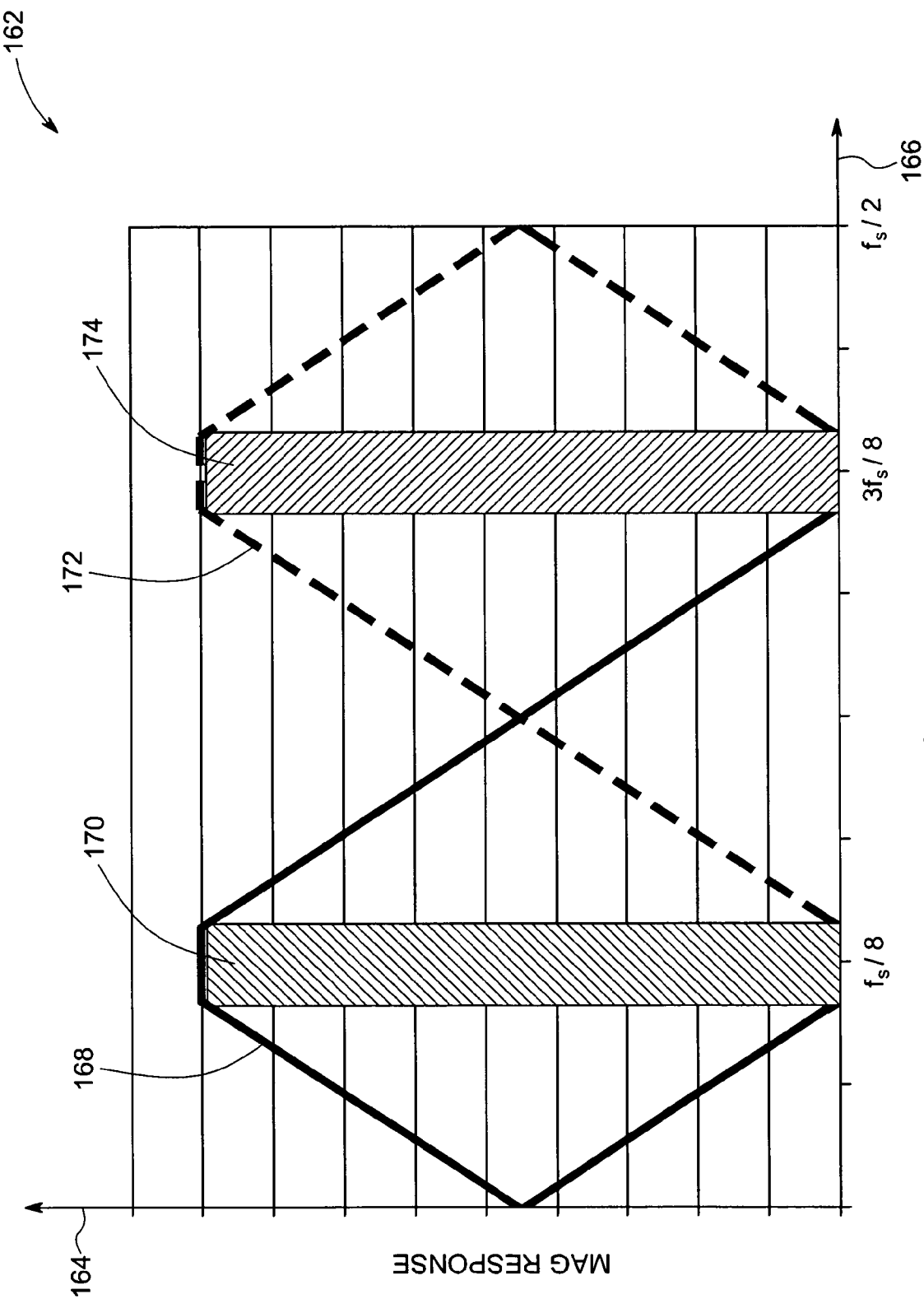
FIG. 6 is an illustration of signal responses of two receiving antennas of the system illustrated in FIG. 3, according to aspects of the present technique.

Considering the first and second diversity branches 84, 86 for ease of illustration and assuming that both the first and second receiver front-ends have identically-shaped, symmetric frequency responses, as is depicted in FIG. 6, the frequencies $f_1$ and $f_2$ may be chosen to be:

$$f_1 = \frac{f_s}{8} \qquad (2)$$

and $$f_2 = \frac{3f_s}{8}.$$

This choice of frequencies facilitates situating the two band copies at maximum separation from each other and from their own aliased tails in the Nyquist range of the ADC. For this scheme, the composite front-end selectivity may be chosen to be sufficient to limit an $$\pm \frac{f_s}{4}$$

out-of-band interferer less than ($P_{weak}$–$SIR_{min}$), where $P_{weak}$ is the power level of the weakest signal to be received, and $SIR_{min}$ is the minimum acceptable signal to interference ratio.

If high dynamic range is desired and strong interferers are expected at $$\pm \frac{f_s}{4}$$

large guard bands may be employed. This in turn facilitates reduction in the number of separate signals which may be frequency multiplexed to a single ADC in the embodiment illustrated in FIG. 3 due to finite Nyquist range. Using highly selective RF front-ends may mitigate this problem but physically large, complex, and costly custom analog bandpass filters may disadvantageously outweigh the savings of fewer ADCs. In particular, as illustrated in FIG. 7, incorporating analog notch (band stop) filters at center $$\pm \frac{f_s}{4}$$

(for the case of two signal FDM) may be advantageous. Such notch filtering could be done at RF, IF or both.

FIG. 6 illustrates the identically shaped, symmetric frequency responses 162 of the two diversity branches 84, 86 (see FIG. 3). In FIG. 6, the amplitude 164 of the frequency responses of the two receiving antennas 90, 104 (see FIG. 3) is plotted against the frequencies 166. Reference numeral 166 illustrates the actual frequency response of the first receiving antenna 90, while a desired response of the first receiving antenna 90 is represented by reference numeral 170. Similarly, reference numeral 172 illustrates the actual frequency response of the second receiving antenna 104, while a desired response of the second receiving antenna 104 is represented by reference numeral 174.

Figure 7:
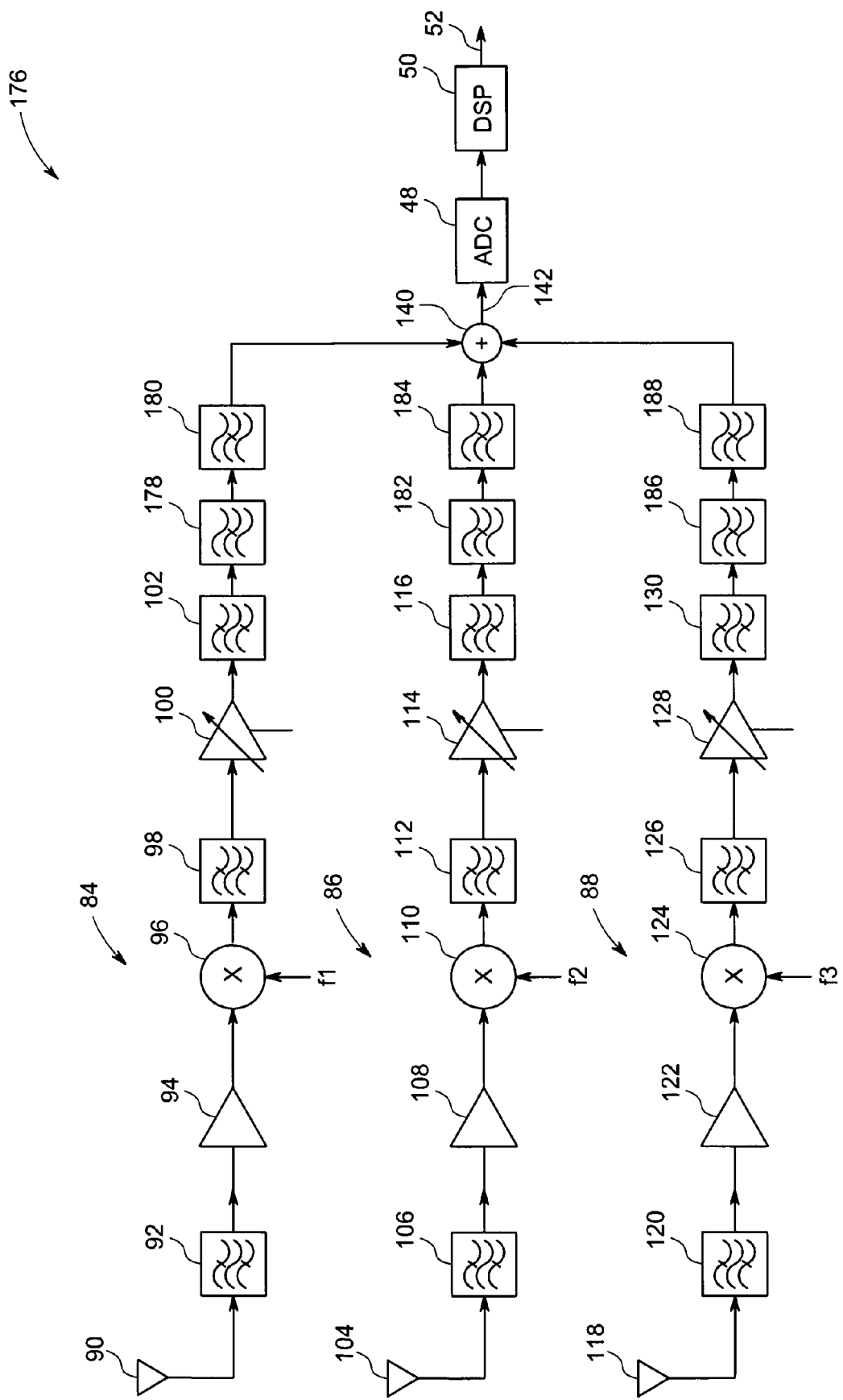
FIG. 7 is a schematic illustration of an alternative embodiment of the embodiment illustrated in FIG. 3, according to aspects of the present technique.

FIG. 7 illustrates an alternate embodiment 176 of the frequency multiplexing system 82 illustrated in FIG. 3. In this embodiment, each of the first, second and third diversity branches 84, 86, 88 includes one or more notch filters. As will be appreciated, the notch filter may be a band reject filter that is configured to attenuate one frequency band and pass both a lower and a higher frequency band. In a presently contemplated configuration illustrated in FIG. 7, the first diversity branch 84 is shown as having a first notch filter 178 and a second notch filter 180. Similarly, the second diversity branch 86 is illustrated as having a first notch filter 182 and a second notch filter 184. As with the first and second diversity branches 84, 86, the third diversity branch 88 may include a first notch filter 186 and a second notch filter 188. Each of the plurality of notch filters may be configured to provide additional attenuation at IF frequencies $$\pm \frac{f_s}{4}$$

thereby advantageously easing the burden on the respective bandpass filters.

Figure 8:
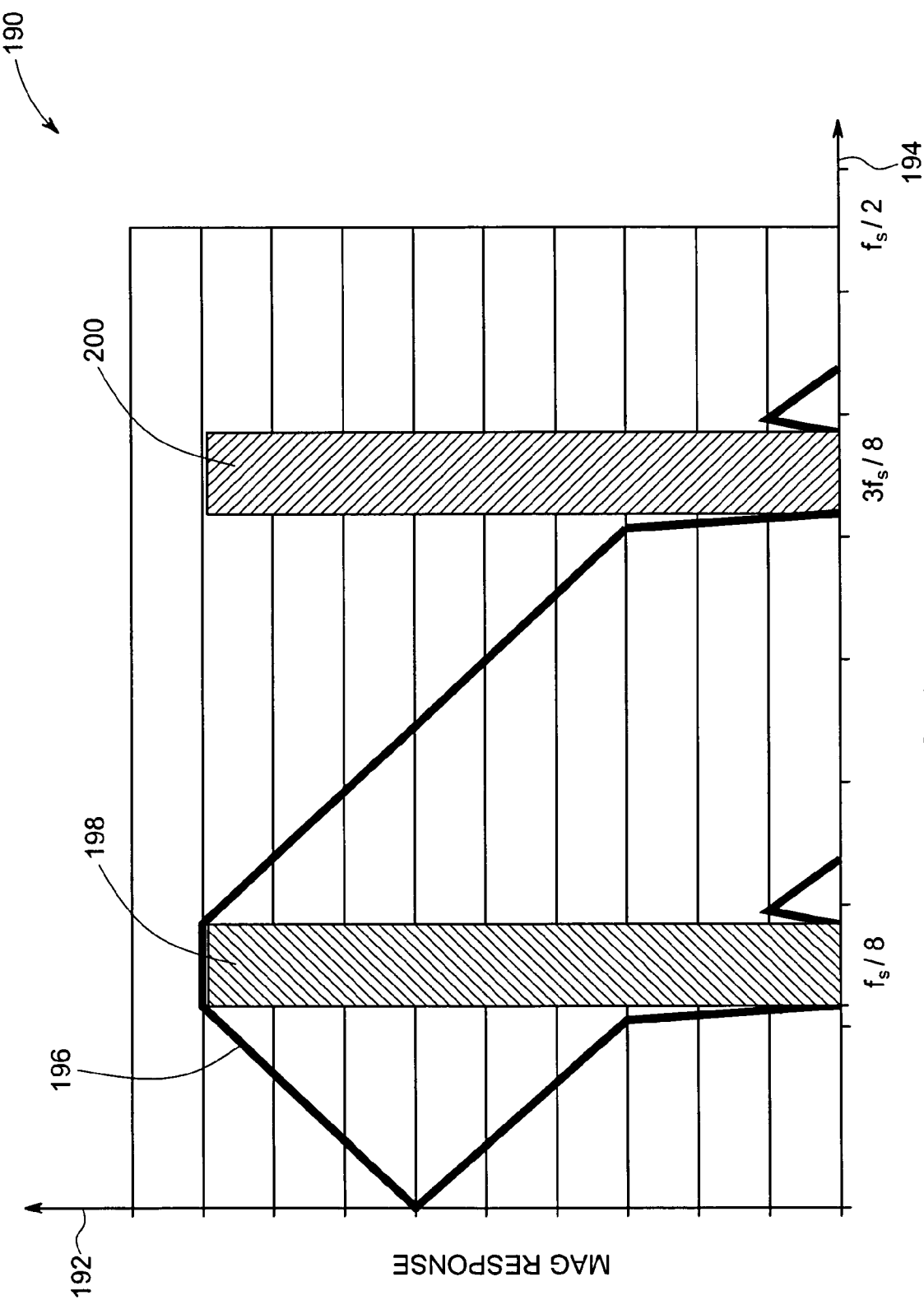
FIG. 8 is an illustration of signal responses of one receiving antenna of the system illustrated in FIG. 7, according to aspects of the present technique.

FIG. 8 illustrates a frequency response 190 of the one diversity branch, such as the first diversity branch 84, of the system illustrated in FIG. 7. In FIG. 8, the amplitude 192 of the frequency response of the receiving antenna 90 (see FIG. 7) is plotted against the frequency 194. Reference numeral 196 illustrates the actual frequency response of the first receiving antenna 90, while a desired response of the first receiving antenna 90 is represented by reference numeral 198. A desired response of the second receiving antenna 104 is represented by reference numeral 200.

As previously noted, the WMTS spectrum consists of three disjoint bands totaling 16 MHz: UHF (608-614 MHz), lower L-band (1395-1400 MHz) and upper L-band (1427-1432 MHz). Accordingly, in the antenna diversity illustrated in FIG. 3, the desired signal may be transmitted over one of the three bands mentioned hereinabove. However, as will be appreciated, the desired signal may be transmitted over multiple bands. Consequently, the resulting copies may be separately downconverted to different intermediate frequencies in the RF front-end of the receiver to include desired guard bands based on analog filtering capability. The downconverted copies of the signal may then be simultaneously digitized by a single ADC thereby reducing cost, size, power consumption and complexity. Additionally, the size of the desirable guard bands may be determined based on the quality of analog filtering possible in the RF front-ends.

Figure 9:
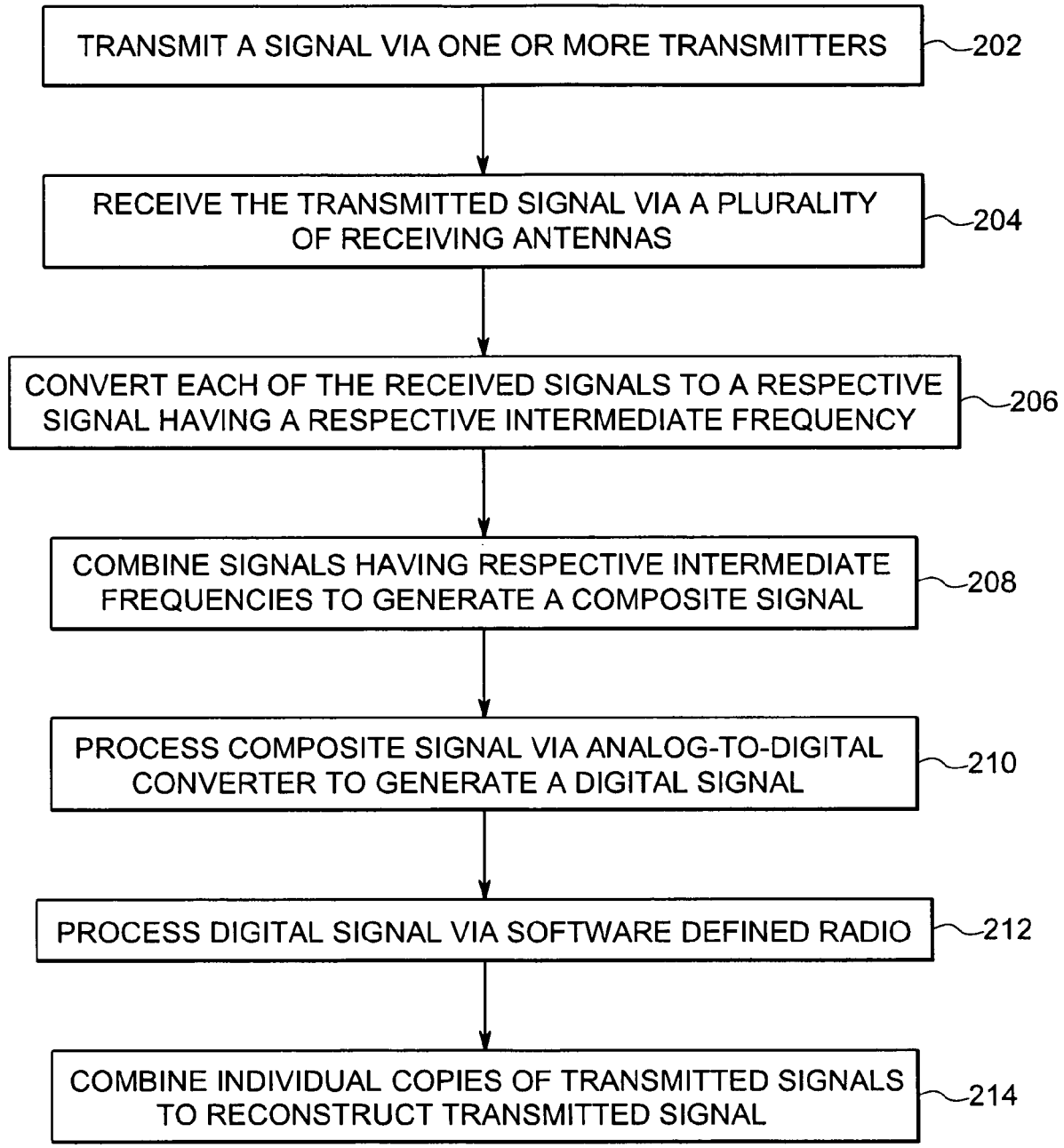
FIG. 9 is a flow chart illustrating an exemplary process of communicating signals, according to aspects of the present technique.

Referring now to FIG. 9, a flow chart depicting an exemplary method for communicating signals, in accordance with aspects of the present technique, is illustrated. The method summarized in FIG. 9 begins at step 202. In step 202, an information-bearing signal generated by a data source 12 (see FIG. 1) may be transmitted via one or more transmitters. For example, the information-bearing signal generated by the data source 12 may be transmitted via the first and second transmitters 14, 18 at two different frequencies, as previously noted. Subsequently, the two copies of the transmitted signal may be received at a plurality of receiving antennas at step 204. For example, each of the receiving antennas 90, 104, 118 (see FIG. 3) may be configured to receive the two copies of the transmitted signal. Thus, in the illustrated embodiment of FIG. 3, six copies of the transmitted signals are received at the receivers 90, 104, 118.

At step 206, each of the received signals may be processed via a respective diversity branch, such as diversity branches 84, 86, 88. Consequent to the processing via each respective diversity branch, each of the received signals may be downconverted to a signal having a respective intermediate frequency, as previously described. For example, the two copies of the signal received at the first receiver 90 may be downconverted to signals having first and second intermediate frequencies. In addition, a signal-to-noise ratio may be computed for the first received signal. Also, a signal power of the first received signal may be estimated at step 206. Similarly, the signals received at the second and third antennas 104, 118 may be downconverted to respective intermediate frequencies. Further, signal-to-noise ratios and signal powers associated with each of the signals may also be computed at step 206.

Subsequently, at step 208, the signals having respective intermediate frequencies may be added via the adder 140 (see FIG. 3) to generate a single, composite analog signal, such as composite signal 142 (see FIG. 4). As previously noted, the downconverted signals may be distributed over the composite signal 142. The signals having respective intermediate frequencies may be separated by a suitable dead band that may be required by analog selection filters, such as the bandpass filters.

At step 210, the composite analog signal 142 may be processed by a single ADC to generate a digital signal. In one embodiment, the composite analog signal may be sampled at a high rate by the ADC. Alternatively, the composite analog signal may be undersampled, and the remodulation frequencies may be arranged such that aliased versions of the received signals remain separate in frequency in the digital signal.

Subsequently, at step 212, the digital output from the single ADC may then be further processed via a software defined radio or software radio to extract individual copies of the signal transmitted by a respective transmitter, as previously described. Further, at step 214, the individual copies of signals transmitted by a respective transmitter may be combined to reconstruct the transmitted signal. In certain embodiments, the software radio may be configured to coherently combine the signal components having the first, second and third intermediate frequency in the digital output. Alternatively, the software radio may be configured to select one of the three intermediate frequency components.

In accordance with aspects of the present technique, decisions about how to process the signal components via the software radio may be made at any time in response to suitable criteria. In one embodiment, the decision about how to process the signal components may be dependent on the respective estimated signal-to-noise ratio values of the signal components having first, second and third intermediate frequencies. Alternatively, in certain other embodiments, the decision may be based on other criteria such as the estimated signal power of the signals having the first and second intermediate frequencies.

The digital output of the ADC includes three received copies of the single transmitted signal. Subsequently, these three copies may then be combined via the software radio. The software radio may be employed to facilitate demodulating the combined signal to produce a baseband signal that is representative of the desired transmitted information. In one embodiment, the three copies may be combined based upon the computed respective signal-to-noise ratios. Alternatively, the three copies of the transmitted signal may be coherently combined via maximal ratio combining. As will be appreciated, maximal ratio combiner is defined as a diversity combiner in which the signals from each channel are added together, the gain of each channel is made proportional to the root means squared (RMS) signal level and inversely proportional to the mean square noise level in that channel, and the same proportionality constant is used for all channels. Further, a diversity combiner is a circuit or device for combining two or more signals carrying the same information received via separate paths or channels with the objective of providing a single resultant signal that is superior in quality to any of the contributing signals.

Figure 10:
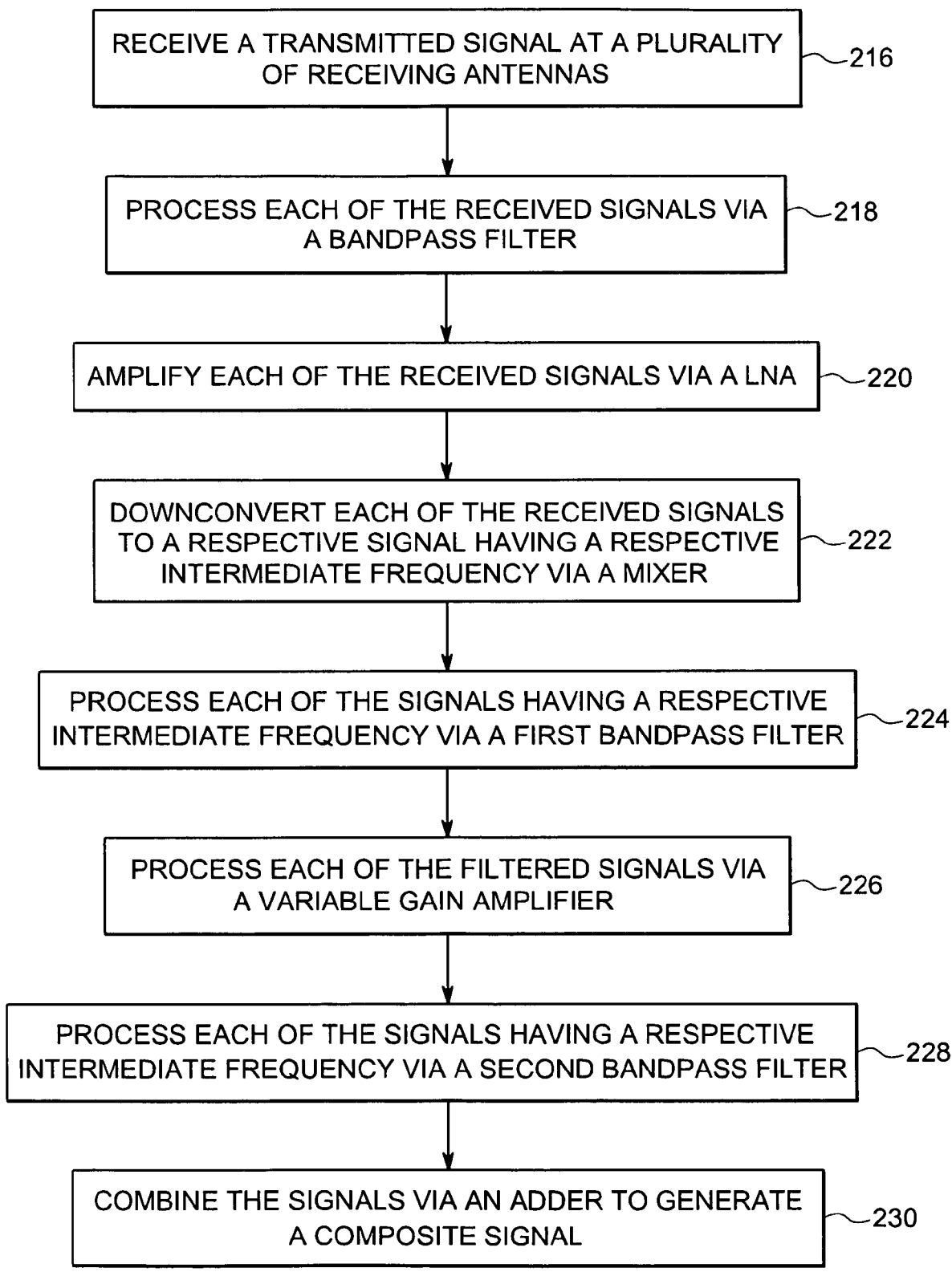
FIG. 10 is a flow chart illustrating an exemplary process of combining analog signals, according to aspects of the present technique.

Turning now to FIG. 10, a flow chart illustrating an exemplary process for combining received signals is depicted. The method begins at step 216 where the transmitted signal is received at a plurality of receiving antennas such as receiving antennas 90, 104, 118 (see FIG. 3). Each of the received signals may be processed via a respective SAW filter, such as SAW filters 92, 106, 120 (see FIG. 3) at step 218. Further, at step 220, each of the filtered signals may be amplified via a respective LNA, such as LNAs 94, 108, 122 (see FIG. 3) to enhance any weak signals. Subsequently, at step 222, each of the received signals may be translated or downconverted to a respective signal having a respective intermediate frequency. As previously described, each of the received signals may be downconverted to a signal having a respective intermediate frequency by mixing each of the received signals with a signal generated by a local oscillator. These downconverted signals may then be processed by a first set of bandpass filters, such as bandpass filters 98, 112, 126 (see FIG. 3) at step 224. The filtering step may be followed by processing each of the filtered signals via a variable gain amplifier, such as variable gain amplifiers 100, 114, 128 (see FIG. 3) at step 226. Subsequently, the signals may be filtered by a second set of bandpass filters, such as bandpass filters 102, 116, 130 at step 228. Following step 228, these downconverted received signals may then be combined via an adder, such as adder 140 (see FIG. 3) to generate a single composite analog signal at step 230. The composite signal, such as composite signal 142 (see FIG. 4), includes a remodulated spectrum, where the copies of the transmitted signal, such as transmitted signals 132, 134, 136, have been translated to a different portion of the baseband spectrum.

Figure 11:
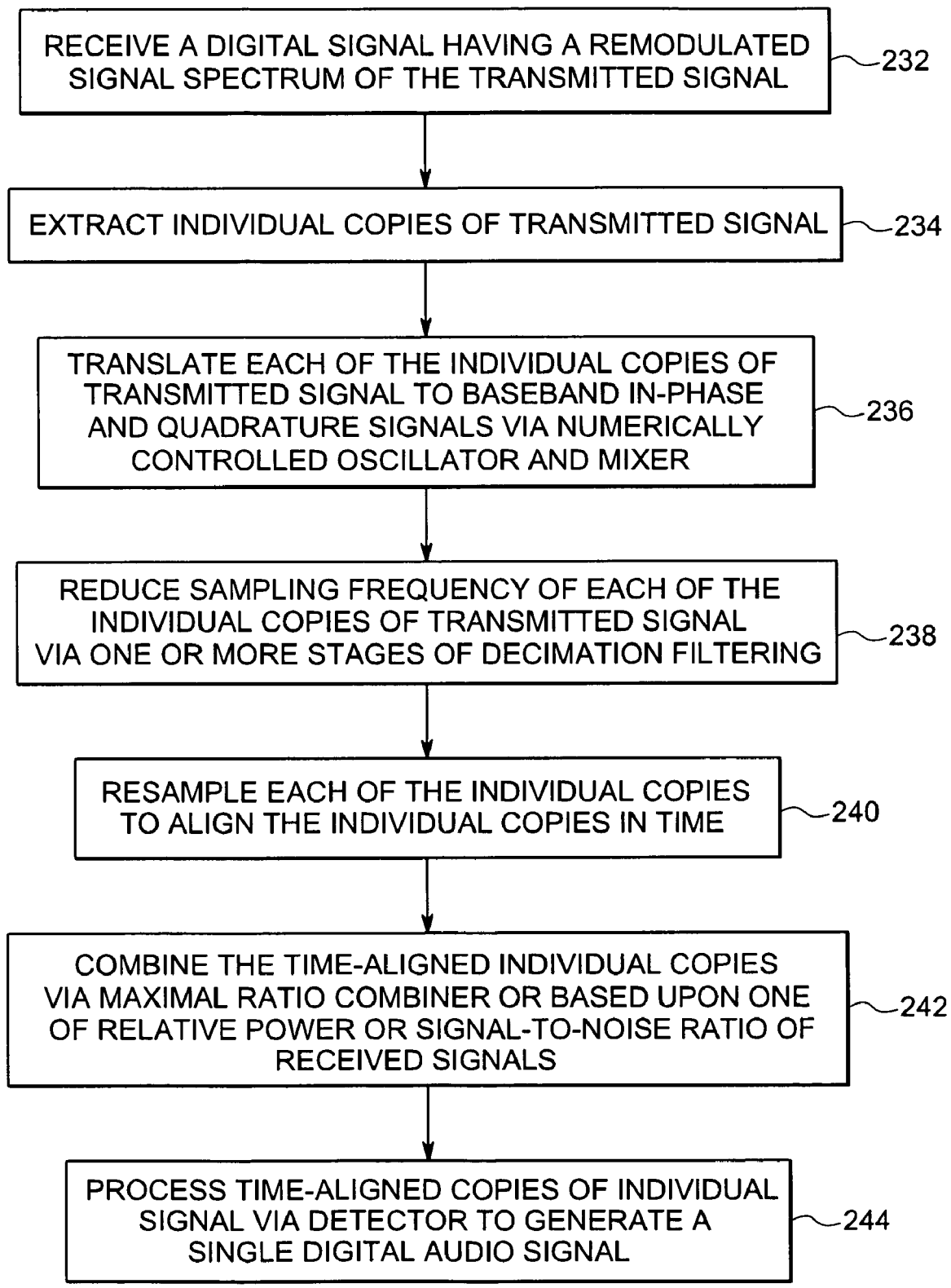
FIG. 11 is a flow chart illustrating an exemplary process of combining digital signals, according to aspects of the present technique.

FIG. 11 is a flow chart illustrating an exemplary process of combining digital signals in the software radio 50 (see FIG. 5) of the DSP module 50 (see FIG. 3). The method begins at step 232, where a digital signal having a remodulated signal spectrum is received at the software radio 50 (see FIG. 3) from the ADC 48 (see FIG. 3). At step 234, individual narrowband copies of the signal transmitted by a given transmitter, such as transmitter 14 (see FIG. 1), may be extracted from the digital signal. Further, at step 236, each of the individual copies of the transmitted signal may be translated to baseband in-phase (I) and quadrature (Q) signals by the numerically controlled oscillator 150 and digital mixer 148 (see FIG. 5), as previously described. Subsequently, at step 238, one or more stages of decimation filtering may be applied to the I and Q signals to reduce the sampling rate to an appropriate frequency for baseband operation, as previously noted.

Each of the individual copies of the transmitted signals is received at the receiving antennas at different phases, as previously noted. Consequently, the individual copies of the transmitted signal are shifted in time. It is desirable to align these time shifted signals prior to combining each of the individual copies of the transmitted signal. At step 240, each of the individual copies may be aligned in time. In certain embodiments, the time-alignment may include time shifts of less than one sample period.

Following step 240, each of the time-aligned individual copies may be combined to generate one signal representative of the signal transmitted via a given transmitter at step 242. As previously noted, the individual copies may be combined based upon a signal-to-noise ratio or estimated signal power. Alternatively, the individual copies may be coherently combined via a maximal ratio combiner. The combined signal may then be processed via a detector to generate a single digital audio signal at step 244.

The various communication systems and the methods of communicating signals described hereinabove facilitate enhanced performance of the wireless communication systems. Further, employing the techniques of communicating signals described hereinabove facilitates building cost effective wireless communication systems due to the reduction of high cost RF chains that include elements such as, but not limited to, analog-to-digital converters, low noise amplifiers, and downconverters. In addition, employing the methods described hereinabove, all of the antenna field signals for each transmission channel are available for simultaneous processing thereby enabling use of techniques such as maximal ratio combining rather than selection of antennas. Consequently, the antenna field switching is less time critical as the antenna fields may be switched at any time.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A system comprising:
   one or more transmitters, wherein each of the one or more transmitters is configured to transmit a signal, and wherein the signal transmitted by each of the one or more transmitters corresponds to a different frequency;
   plurality of receiver front-ends configured to receive the signal transmitted by each of the one or more transmitters;
   a plurality of remodulator modules configured to translate each of the received signals to a signal having a respective intermediate frequency;
   a combining module configured to combine each of the signals having respective intermediate frequencies to generate a single composite signal;
   a single analog-to-digital converter configured to process the composite signal and generate a digital output; and
   a digital signal processor module configured to extract the signal transmitted by each of the one or more transmitters.

2. The system of claim 1, further comprising a data source configured to generate a data signal.

3. The system of claim 2, wherein the, data signal comprises electrocardiogram data, blood pressure data, blood oxygen level data, or combinations thereof.

4. The system of claim 1, wherein the system comprises a telemetry system.

5. The system of claim 4, wherein the telemetry system comprises a medical telemetry system.

6. The system of claim 1, wherein each of the one or more transmitters is configured to transmit a data signal at a predetermined frequency range, wherein the predetermined frequency range varies from about 608 MHz to about 614 MHz, from about 1395 MHz to about 1400 MHz, from about 1427 MHz to about 1432 MHz, or combinations thereof.

7. The system of claim 6, wherein each of the one or more transmitters is configured to modulate the data signal using a modulation technique, wherein the modulation technique comprises one of a minimum shift keying, Gaussian minimum shift keying, frequency shift keying, differential frequency shift keying or Gaussian frequency shift keying.

8. The system of claim 1, wherein the digital signal processor module comprises a software defined radio configured to extract individual copies of the signal transmitted by each of the one or more of transmitters.

9. A method of communicating signals, the method comprising:
   transmitting a signal via one or more transmitters, wherein each of the one or more transmitters is configured to transmit the signal at a respective frequency;
   receiving the transmitted signal via a plurality of receiver front-ends;
   converting each of the received signals to a respective signal having a respective intermediate frequency;
   combining each of the signals having respective intermediate frequencies to generate a single composite analog signal;
   processing the composite analog signal via an analog-to-digital converter to generate a digital output signal;
   processing the digital signal via a digital signal processor module to extract the signal transmitted by each of the one or more transmitters; and
   combining the individual copies of each of the transmitted signals to reconstruct the transmitted signal.

10. The method of claim 9, further comprising generating a data signal via a data source for transmittal via the one or more transmitters.

11. The method of claim 9, wherein the step of receiving comprises:
    filtering and amplifying the received signals; and
    estimating a signal-to-noise ratio and relative power of each of the received signals.

12. The method of claim 9, wherein the step of converting comprises:
    translating each of the received signals to a signal having an intermediate frequency by mixing each of the received signals with a respective radio frequency signal generated by a local oscillator; and
    processing each of the translated signals via a first bandpass filter, a variable gain amplifier and a second bandpass filter.

13. The method of claim 9, wherein the step of combining each of the signals having respective intermediate frequencies to generate a single composite analog signal comprises combining each of translated signals via an adder.

14. The method of claim 9, wherein the step of processing the digital signal via a digital signal processor module comprises processing the digital signal via a software defined radio, wherein the software defined radio is configured to extract the signal transmitted by each of the one or more transmitters.

15. The method of claim 14, wherein processing the digital signal via the software defined radio comprises:
    extracting individual copies of the signal transmitted by each of the one or more transmitters;
    translating each of the individual copies to baseband via a numerically controlled oscillator and a mixer;
    reducing sampling frequency of each of the individual copies via one or more stages of decimation filtering; and
    resampling each of the decimation filtered individual copies to align each of the individual copies in time.

16. The method of claim 9, wherein the step of combining the individual copies of each of the transmitted signals comprises combining time-aligned individual copies of the transmitted signal based upon respective relative powers or respective signal-to-noise ratios of the received signals.

17. The method of claim 9, wherein the step of combining the individual copies of each of the transmitted signals comprises coherently combining time-aligned individual copies of the transmitted signal via a maximal ratio combiner.

18. The method of claim 9, further comprising processing time-aligned copies of each of the transmitted signals via a detector to generate a single digital output signal.

19. The system of claim 1, wherein the plurality of receiver front-ends are displaced at different positions.

20. The system of claim 1, further comprising a mixer configured to obtain an intermediate frequency signal.

21. The system of claim 1, wherein the composite signal range varies from about 30 MHz to about 62.5 MHz.

* * * * *

UNITED STATES PATENT AND TRADEMARK OFFICE
CERTIFICATE OF CORRECTION

PATENT NO. : 7,573,398 B2
APPLICATION NO. : 11/171173
DATED : August 11, 2009
INVENTOR(S) : Hoctor et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 598 days.

Signed and Sealed this

Seventh Day of September, 2010

David J. Kappos
*Director of the United States Patent and Trademark Office*